(12) United States Patent
Hong et al.

(10) Patent No.: US 10,087,371 B2
(45) Date of Patent: Oct. 2, 2018

(54) LIQUID CRYSTAL COMPOSITION AND LIQUID CRYSTAL DISPLAY INCLUDING THE SAME

(71) Applicant: SAMSUNG DISPLAY CO., LTD., Yongin-si, Gyeonggi-do (KR)

(72) Inventors: Sung-Hwan Hong, Suwon-si (KR); Hoi-Lim Kim, Seoul (KR); Da Hye Cho, Hwaseong-si (KR); Young Mi Cho, Seoul (KR)

(73) Assignee: SAMSUNG DISPLAY CO., LTD., Yongin-si, Gyeonggi-do (KR)

( * ) Notice: Subject to any disclaimer, the term of this patent is extended or adjusted under 35 U.S.C. 154(b) by 0 days.

(21) Appl. No.: 15/407,699

(22) Filed: Jan. 17, 2017

(65) Prior Publication Data
US 2017/0204331 A1 Jul. 20, 2017

(30) Foreign Application Priority Data
Jan. 20, 2016 (KR) .................. 10-2016-0007007

(51) Int. Cl.
| | | |
|---|---|---|
| *G02F 1/1333* | (2006.01) | |
| *C09K 19/32* | (2006.01) | |
| *C07C 43/192* | (2006.01) | |
| *C07C 25/22* | (2006.01) | |
| *G02F 1/1368* | (2006.01) | |
| *G02F 1/1343* | (2006.01) | |
| *G02F 1/137* | (2006.01) | |

(52) U.S. Cl.
CPC ............ *C09K 19/322* (2013.01); *C07C 25/22* (2013.01); *C07C 43/192* (2013.01); *G02F 1/137* (2013.01); *G02F 1/1368* (2013.01); *G02F 1/13439* (2013.01); *G02F 1/134309* (2013.01); *C07C 2103/16* (2013.01); *G02F 2001/13712* (2013.01); *G02F 2001/134345* (2013.01); *G02F 2201/121* (2013.01); *G02F 2201/123* (2013.01); *G02F 2202/42* (2013.01)

(58) Field of Classification Search
CPC ......... G02F 1/1333; G02F 1/1368; G02F 1/134309; G02F 1/13439; G02F 1/137; G02F 2001/13712; G02F 2001/134345; G02F 2201/123; G02F 2201/121; G02F 2202/42; C09K 19/322; C07C 43/192; C07C 25/22; C07C 2103/16
USPC .................. 252/299.01, 299.63; 428/1.1
See application file for complete search history.

(56) References Cited

U.S. PATENT DOCUMENTS

| | | | |
|---|---|---|---|
| 7,575,785 B2* | 8/2009 | Lietzau ............... | C07C 17/093 252/299.62 |
| 8,801,966 B2 | 8/2014 | Chen et al. | |
| 2003/0108684 A1* | 6/2003 | Hornung ............... | C07C 25/22 428/1.1 |
| 2006/0165915 A1 | 7/2006 | Lietzau et al. | |
| 2006/0202163 A1 | 9/2006 | Lietzau et al. | |
| 2008/0071097 A1 | 3/2008 | Taugerbeck et al. | |
| 2010/0059711 A1 | 3/2010 | Kretzschmann et al. | |
| 2013/0310558 A1 | 11/2013 | Brummond et al. | |

FOREIGN PATENT DOCUMENTS

KR    10-2009-0040902 A    4/2009

OTHER PUBLICATIONS

Gwozdz, et al. "Influence of Dipole-Dipole Interactions on Structural Properties of Gay-Berne Particles", Acta Physica Polonica A No. 5 vol. 95 (2000) pp. 645-649.

* cited by examiner

*Primary Examiner* — Geraldina Visconti
(74) *Attorney, Agent, or Firm* — Lee & Morse, P.C.

(57) ABSTRACT

A liquid crystal composition and a liquid crystal display, the composition including a liquid crystal compound represented by Chemical Formula 1 below:

Chemical Formula 1

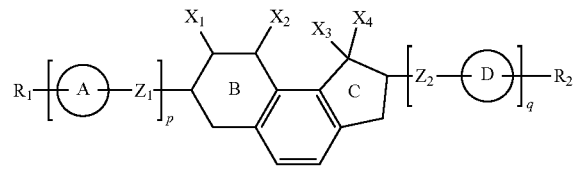

16 Claims, 2 Drawing Sheets

LIQUID CRYSTAL COMPOSITION AND LIQUID CRYSTAL DISPLAY INCLUDING THE SAME

CROSS-REFERENCE TO RELATED APPLICATION

Korean Patent Application No. 10-2016-0007007, filed on Jan. 20, 2016, in the Korean Intellectual Property Office, and entitled: "Liquid Crystal Composition and Liquid Crystal Display Including the Same," is incorporated by reference herein in its entirety.

BACKGROUND

1. Field

Embodiments relate to a liquid crystal composition and a liquid crystal display including the same.

2. Description of the Related Art

A liquid crystal display (LCD) is one among widely-used display devices. The liquid crystal display may have two display panels on which field generating electrodes, such as pixel electrodes and a common electrode, are formed, and a liquid crystal layer that is interposed between the display panels. In the liquid crystal display, a voltage may be applied to the field generating electrodes so as to form an electric field in the liquid crystal layer, the alignment of liquid crystal molecules of the liquid crystal layer may be determined by the electric field, and the polarization of incident light may be controlled.

The above information disclosed in this Background section is only for enhancement of understanding of the background of the invention and therefore it may contain information that does not form the prior art that is already known in this country to a person of ordinary skill in the art.

SUMMARY

Embodiments are directed to a liquid crystal composition and a liquid crystal display including the same.

The embodiments may be realized by providing a liquid crystal composition comprising a liquid crystal compound represented by Chemical Formula 1 below:

Chemical Formula 1 wherein, in Chemical Formula 1, $X_1$ to $X_4$ are each independently hydrogen, fluorine, or an alkyl group, $Z_1$ and $Z_2$ are each independently a single bond, a double bond, $CF_2CF_2$, or $OCF_2$, $R_1$ is hydrogen, fluorine, or an alkyl group, $R_2$ is hydrogen, fluorine, an alkyl group, or an alkoxy group, A is , or D is , or

B is cyclohexane, cyclohexene, or benzene, C is cyclopentane or cyclopentene, $X_5$, $X_6$, $X_7$, and $X_8$ in A and D are each independently hydrogen, fluorine, or an alkyl group, p is an integer of 1 to 4, q is an integer of 0 to 3, and n is an integer of 1 to 4.

The liquid crystal compound represented by Chemical Formula 1 may include a liquid crystal compound represented by one of Chemical Formula 1-1 to 1-4:

Chemical Formula 1-1

Chemical Formula 1-2

Chemical Formula 1-3

Chemical Formula 1-4

A dielectric anisotropy (Δ∈) of the liquid crystal compound represented by Chemical Formula 1 may be −4 to −5, and a rotation viscosity (γ1) of the liquid crystal compound represented by Chemical Formula 1 may be about 150 or less.

A phase transition temperature (Tni) of the liquid crystal compound represented by Chemical Formula 1 may be 95° C. to 105° C., and a refractive anisotropy (Δn) of the liquid crystal compound represented by Chemical Formula 1 may be 0.2 to 0.3.

The liquid crystal composition may further include a liquid crystal compound represented by one of Chemical Formula 2 to Chemical Formula 19:

Chemical Formula 2

Chemical Formula 3

Chemical Formula 4

Chemical Formula 5

Chemical Formula 6

Chemical Formula 7

Chemical Formula 8

Chemical Formula 9

Chemical Formula 10

Chemical Formula 11

Chemical Formula 12

Chemical Formula 13

Chemical Formula 14

Chemical Formula 15

Chemical Formula 16

Chemical Formula 17

Chemical Formula 18

Chemical Formula 19 wherein, in Chemical Formula 2 to Chemical Formula 19, X and Y are each independently a C1 to C4 alkyl group.

A dielectric anisotropy (Δ∈) of the liquid crystal composition may be −3 to −4.

A rotation viscosity (γ1) of the liquid crystal composition may be about 120 or less.

The embodiments may be realized by providing a liquid crystal display including a first substrate; a second substrate separated from and overlapping the first substrate; and a liquid crystal layer positioned between the first substrate and the second substrate, wherein the liquid crystal layer includes a liquid crystal compound represented by Chemical Formula 1:

Chemical Formula 1 wherein, in Chemical Formula 1, $X_1$ to $X_4$ are each independently hydrogen, fluorine, or an alkyl group, $Z_1$ and $Z_2$ are each independently a single bond, a double bond, $CF_2CF_2$, or $OCF_2$, $R_1$ is hydrogen, fluorine, or an alkyl group, $R_2$ is hydrogen, fluorine, an alkyl group, or an alkoxy group, A is D is

B is cyclohexane, cyclohexene, or benzene, C is cyclopentane or cyclopentene, $X_5$, $X_6$, $X_7$, and $X_8$ in A and D are each independently hydrogen, fluorine, or an alkyl group, p is an integer of 1 to 4, q is an integer of 0 to 3, and n is an integer of 1 to 4.

The liquid crystal compound represented by Chemical Formula 1 may include a liquid crystal compound represented by one of Chemical Formula 1-1 to 1-4:

Chemical Formula 1-1

Chemical Formula 1-2

Chemical Formula 1-3

Chemical Formula 1-4

A dielectric anisotropy (Δ∈) of the liquid crystal compound represented by Chemical Formula 1 may be −4 to −5, and a rotation viscosity (γ1) of the liquid crystal compound represented by Chemical Formula 1 may be about 150 or less.

A phase transition temperature (Tni) of the liquid crystal compound represented by Chemical Formula 1 may be 95° C. to 105° C., and a refractive anisotropy (Δn) of the liquid crystal compound represented by Chemical Formula 1 may be 0.2 to 0.3.

The liquid crystal layer may further include a liquid crystal compound represented by one of Chemical Formula 2 to Chemical Formula 19:

Chemical Formula 2

Chemical Formula 3

Chemical Formula 4

Chemical Formula 5

Chemical Formula 6

Chemical Formula 7

Chemical Formula 8

Chemical Formula 9

Chemical Formula 10

Chemical Formula 11

Chemical Formula 12

Chemical Formula 13

Chemical Formula 14

Chemical Formula 15

Chemical Formula 16

Chemical Formula 17

Chemical Formula 18

Chemical Formula 19 wherein, in Chemical Formula 2 to Chemical Formula 19, X and Y are each independently a C1 to C4 alkyl group.

A dielectric anisotropy ($\Delta\epsilon$) of the liquid crystal composition may be −3 to −4.

A rotation viscosity ($\gamma1$) of the liquid crystal composition may be about 120 or less.

The liquid crystal display may further include a thin film transistor on the first substrate; a pixel electrode connected to the thin film transistor; and a common electrode forming an electric field with the pixel electrode.

The pixel electrode may include a cross-shaped stem and a minute branch extending from the cross-shaped stem.

BRIEF DESCRIPTION OF THE DRAWINGS

Features will be apparent to those of skill in the art by describing in detail exemplary embodiments with reference to the attached drawings in which.

DETAILED DESCRIPTION

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. Like reference numerals refer to like elements throughout.

It will be understood that when an element such as a layer, film, region, or substrate is referred to as being "on" another element, it can be directly on the other element or intervening elements may also be present. In contrast, when an element is referred to as being "directly on" another element, there are no intervening elements present. Further, in the specification, the word "on" or "above" means positioned on or below the object portion, and does not necessarily mean positioned on the upper side of the object portion based on a gravitational direction.

In addition, unless explicitly described to the contrary, the word "comprise" and variations such as "comprises," "includes," or "comprising" will be understood to imply the inclusion of stated elements but not the exclusion of any other elements.

Figure 1:
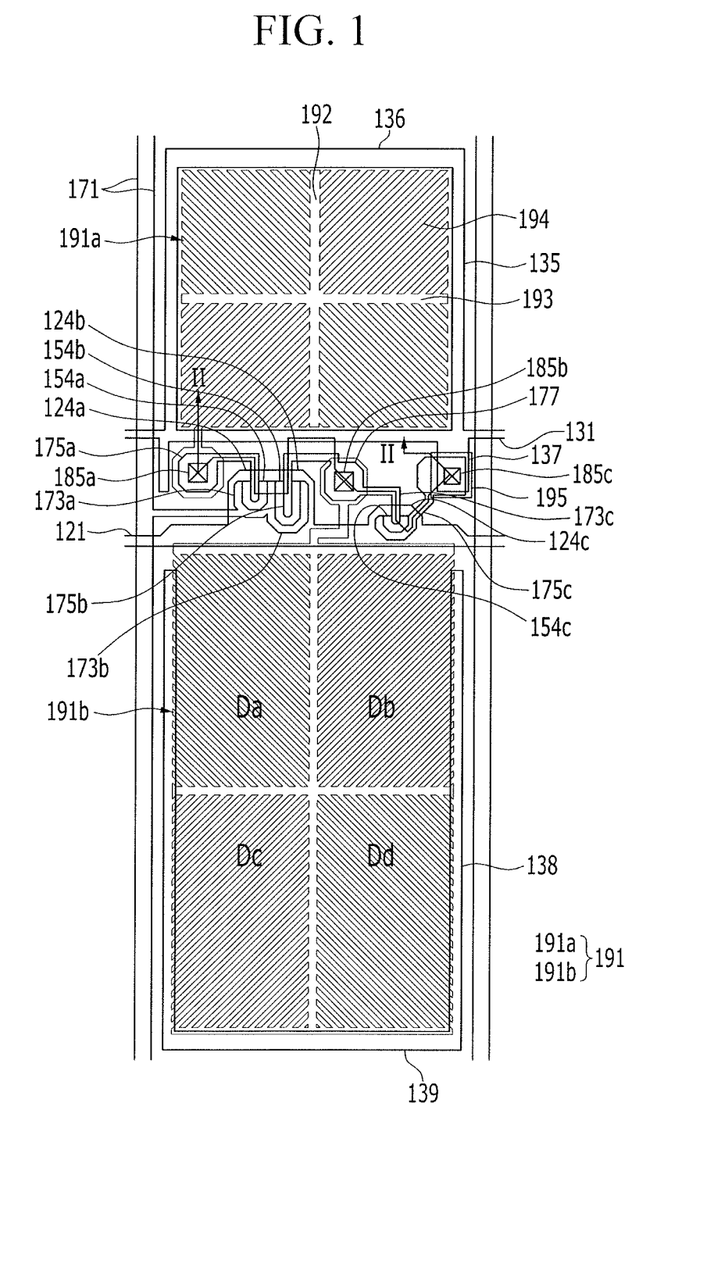
FIG. 1 illustrates a plan layout view of a pixel of a liquid crystal display according to an exemplary embodiment.
Figure 2:
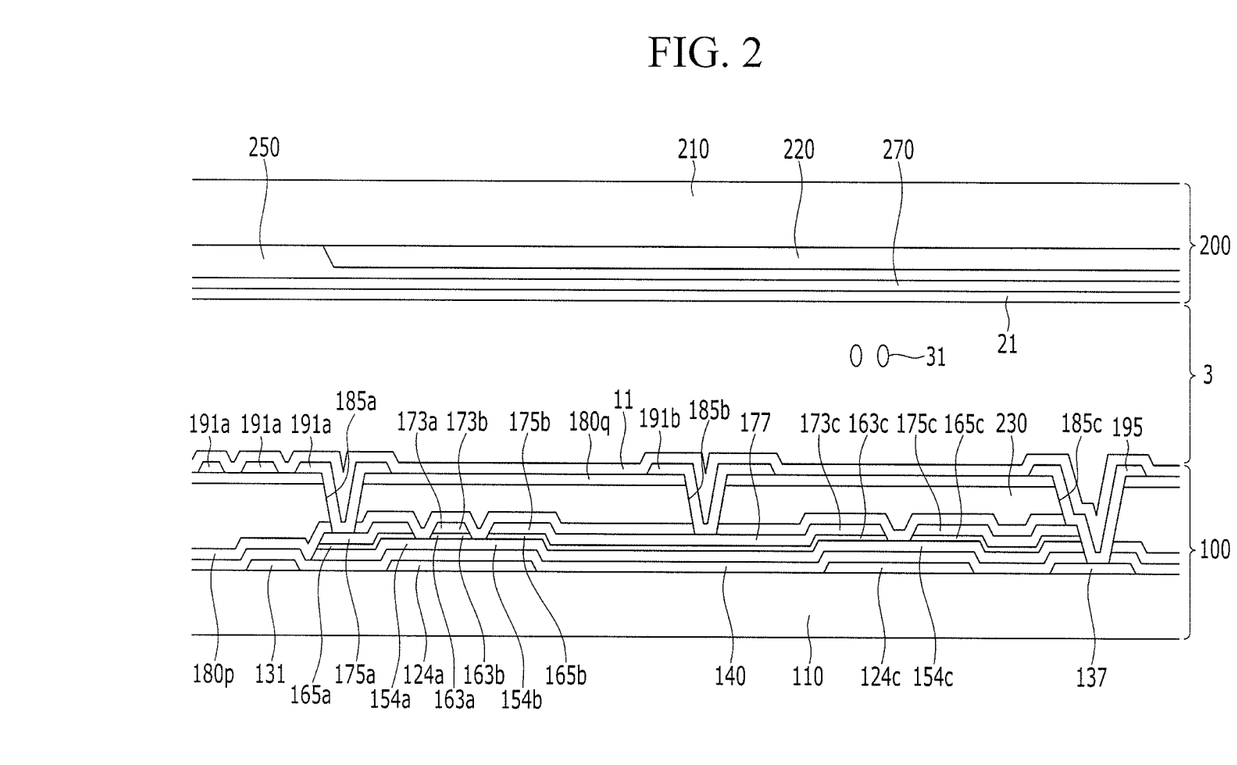
FIG. 2 illustrates a cross-sectional view taken along a line II-II of FIG. 1.

Now, a liquid crystal display according to an exemplary embodiment will be described with reference to FIG. 1 and FIG. 2. FIG. 1 illustrates a plan layout view of a pixel of a liquid crystal display according to an exemplary embodiment, and FIG. 2 illustrates a cross-sectional view taken along a line II-II of FIG. 1.

The liquid crystal display according to an exemplary embodiment may include a lower panel 100, an upper panel 200 facing and separated from the lower panel 100, and a liquid crystal layer 3 positioned between the lower panel 100 and the upper panel 200.

Next, a liquid crystal composition forming the liquid crystal layer 3 according to an exemplary embodiment will be described in detail.

The liquid crystal composition according to an exemplary embodiment may include, e.g., a liquid crystal compound represented by Chemical Formula 1 below.

Chemical Formula 1

In Chemical Formula 1, $X_1$ to $X_4$ may each independently be or include, e.g., hydrogen (H), fluorine (F), or an alkyl group (e.g., $C_nH_{2n+1}$). In an implementation, suitable substituents may be included on any of the described groups. For example, $X_1$ to $X_4$ may each independently be or include, e.g., a methyl group ($CH_3$) or a trifluoromethyl group ($CF_3$). $Z_1$ and $Z_2$ may each independently be or include, e.g., a single bond, a double bond, $CF_2CF_2$, or $OCF_2$. $R_1$ may be or may include, e.g., hydrogen (H), fluorine (F), or an alkyl group (e.g., $C_nH_{2n+1}$). $R_2$ may be or may include, e.g., hydrogen (H), fluorine (F), an alkyl group (e.g., $C_nH_{2n+1}$), or an alkoxy group (e.g., $OC_nH_{2n+1}$). A may be or may include, e.g., D may be or may include, e.g., B may be or may include, e.g., a cyclohexane, a cyclohexene, or a benzene. C may be or may include, e.g., a cyclopentane or a cyclopentene. In an implementation, B may be or may include, e.g., a cyclohexene, or a benzene and/or C may be or may include, e.g., a cyclopentene. For example, B and C may each share a bond with the core benzene moiety shown in Chemical Formula 1 and form a fused ring structure therewith. $X_5$, $X_6$, $X_7$, and $X_8$ in A and D may each independently be or include, e.g., hydrogen (H), fluorine (F), or an alkyl group (e.g., $C_nH_{2n+1}$). p may be, e.g., an integer of 1 to 4, q may be, e.g., an integer of 0 to 3, and n may be, e.g., an integer of 1 to 4.

In an implementation, a dielectric anisotropy (Δ∈) of the liquid crystal compound represented by Chemical Formula 1 may be, e.g., −4 to −5. In an implementation, a rotation viscosity (γ1) of the liquid crystal compound represented by Chemical Formula 1 may be, e.g., about 50 to about 150. Maintaining the rotation viscosity (γ1) of the liquid crystal compound at about 50 or greater may help ensure that a physical property required by the liquid crystal layer is satisfied. In an implementation, a phase transition temperature (Tni) of the liquid crystal compound represented by Chemical Formula 1 may be 95° C. to 105° C. In an implementation, a refractive anisotropy (Δn) of the liquid crystal compound represented by Chemical Formula 1 may be 0.2 to 0.3.

The liquid crystal compound represented by Chemical Formula 1 may be included in the liquid crystal composition in an amount of, e.g., about 1 to 20 wt %, based on a total weight of the liquid crystal composition.

In an implementation, the liquid crystal compound represented by Chemical Formula 1 may include, e.g., a liquid crystal compound represented by one of the following Chemical Formulae 1-1 to 1-4.

Chemical Formula 1-1

Chemical Formula 1-2

Chemical Formula 1-3

Chemical Formula 1-4

The liquid crystal compound represented by Chemical Formula 1-1 to Chemical Formula 1-4 may satisfy the physical properties of the liquid crystal compound represented by Chemical Formula 1. For example, for the liquid crystal compound represented by Chemical Formula 1-1, the refractive anisotropy (Δn) may be 0.258, the dielectric anisotropy (Δ∈) may be −4.25, the rotation viscosity (γ1) may be about 149.6, and the phase transition temperature (Tni) may be 98.4° C. For the liquid crystal compound represented by Chemical Formula 1-2, the refractive anisotropy (Δn) may be 0.249, the dielectric anisotropy (Δ∈) may be −4.83, the rotation viscosity (γ1) may be about 123.3, and the phase transition temperature (Tni) may be 102.9° C. For the liquid crystal compound represented by Chemical Formula 1-3, the refractive anisotropy (Δn) may be 0.267, the dielectric anisotropy (Δ∈) may be −4.22, the rotation viscosity (γ1) may be about 120.5, and the phase transition temperature (Tni) may be 95.2° C. For the liquid crystal compound represented by Chemical Formula 1-4, the refractive anisotropy (Δn) may be 0.258, the dielectric anisotropy (Δ∈) may be −4.83, the rotation viscosity (γ1) may be about 93.3, and the phase transition temperature (Tni) may be 99.7° C.

Referring to the liquid crystal compound represented by Chemical Formula 1, the liquid crystal compound represented by Chemical Formula 1 may include three rings, e.g., fused rings, positioned at a center of a molecular structure. In an implementation, at least one hydrogen (H) connected to the cyclopentane ring or the cyclopentene ring may be substituted with fluorine (F), e.g., one or both of $X_3$ or $X_4$ may be or may include F. In this case, for a phenyl ring adjacent to the C ring (e.g., cyclopentane ring or the cyclopentene ring) and positioned at the center among the three rings, hydrogen connected to the phenyl ring may not be substituted with fluorine (F), etc. If a hydrogen on the phenyl ring were to be substituted or replaced with fluorine, the center of the molecular structure could be formed to be bulky such that the rotation viscosity could increase, and the response speed may be disadvantageous.

For example, for the liquid crystal compound represented by Chemical Formula 1, the phenyl ring structure positioned at the center of the molecular structure may not include fluorine, etc., and the structure of the C ring (e.g., cyclopentane ring or the cyclopentene ring) connected to the phenyl ring may include a fluorine or fluorine-containing substituent. In this case, when including the liquid crystal compound including fluorine on the C ring, the low rotation viscosity may be obtained while obtaining the dielectric anisotropy of the same level.

For example, for the liquid crystal compound represented by Chemical Formula 1-2, the refractive anisotropy (Δn) may be 0.249, the dielectric anisotropy (Δ∈) may be −4.83, the rotation viscosity (γ1) may be about 123.3, and the phase transition temperature (Tni) may be 102.9° C. In contrast, in a liquid crystal compound in which a phenyl ring structure positioned at a center of the molecular structure includes fluorine, e.g., the liquid crystal compound represented by Chemical Formula (1-2a), below, the refractive anisotropy (Δn) may be 0.251, the dielectric anisotropy (Δ∈) may be −4.97, the rotation viscosity (γ1) may be about 224.3, and the phase transition temperature (Tni) may be 91.7° C. For example, the rotation viscosity (γ1) of the liquid crystal compound represented by Chemical Formula 1-2 may be about 50% lower relative to the liquid crystal compound of Chemical Formula (1-2a).

Chemical Formula (1-2a)

Accordingly, the liquid crystal compound according to an exemplary embodiment may have the improved rotation viscosity and improved response speed depending on an application of a voltage.

$$\gamma 1 \approx g \cdot S^2 \cdot \left( \frac{\varepsilon S}{kT} + \frac{\theta S^2}{T - T_0} \right) \quad \text{Equation 1}$$

Equation 1, above, is an equation related to the rotation viscosity (γ1), the rotation viscosity (γ1) being proportional to a square of an order parameter (S), and the order parameter (S) decreases as a dipole moment increases. For example, as the dipole moment increases, the order param- eter (S) may be decreased, and accordingly, the rotation viscosity (γ1) may also be decreased.

In this case, the liquid crystal compound represented by Chemical Formula 1-2 may have a dipole moment of about 0.136, and the liquid crystal compound represented by Chemical Formula (1-2a) may have a dipole moment of about 0.118.

Accordingly, the liquid crystal composition according to an exemplary embodiment may have a high dipole moment compared with another liquid crystal composition, and accordingly the liquid crystal composition may have a low order parameter (S), thereby having a low rotation viscosity (γ1).

In an implementation, the liquid crystal composition according to an exemplary embodiment may further include a liquid crystal compound represented by one of the following Chemical Formula 2 to Chemical Formula 19.

Chemical Formula 2

Chemical Formula 3

Chemical Formula 4

Chemical Formula 5

Chemical Formula 6

Chemical Formula 7

Chemical Formula 8

Chemical Formula 9

Chemical Formula 10

Chemical Formula 11

Chemical Formula 12

Chemical Formula 13

Chemical Formula 14

Chemical Formula 15

Chemical Formula 16

Chemical Formula 17

Chemical Formula 18

Chemical Formula 19

In Chemical Formulae 2 to 19, X and Y may each independently be or include, e.g., an alkyl group (e.g., $C_{n'}H_{2n'+1}$, in which n' in X and Y is independently a natural number of 1 to 4).

In an implementation, the liquid crystal compound represented by Chemical Formula 2 may be included in the composition in an amount of about 10 to 30 wt % for the entire content of the liquid crystal composition (e.g., based on a total weight of the composition). In an implementation, the liquid crystal compound represented by Chemical Formula 3 may be included in the composition in an amount of about 5 to 15 wt % for the entire content of the liquid crystal composition. In an implementation, the liquid crystal compound represented by Chemical Formula 4 may be included in the composition in an amount of about 3 to 10 wt % for the entire content of the liquid crystal composition. In an implementation, the liquid crystal compound represented by Chemical Formula 5 may be included in the composition in an amount of about 10 to 35 wt % for the entire content of the liquid crystal composition. In an implementation, the liquid crystal compound represented by Chemical Formula 6 may be included in the composition in an amount of about 5 to 15 wt % for the entire content of the liquid crystal composition. In an implementation, the liquid crystal compound represented by Chemical Formula 7 may be included in the composition in an amount of about 5 to 15 wt % for the entire content of the liquid crystal composition. In an implementation, the liquid crystal compound represented by Chemical Formula 8 may be included in the composition in an amount of about 3 to 25 wt % for the entire content of the liquid crystal composition. In an implementation, the liquid crystal compound represented by Chemical Formula 9 may be included in the composition in an amount of about 5 to 25 wt % for the entire content of the liquid crystal composition. In an implementation, the liquid crystal compound represented by Chemical Formula 10 may be included in the composition in an amount of about 5 to 20 wt % for the entire content of the liquid crystal composition. In an implementation, the liquid crystal compound represented by Chemical Formula 11 may be included in the composition in an amount of about 5 to 20 wt % for the entire content of the liquid crystal composition. In an implementation, the liquid crystal compound represented by Chemical Formula 12 may be included in the composition in an amount of about 5 to 25 wt % for the entire content of the liquid crystal composition. In an implementation, the liquid crystal compound represented by Chemical Formula 13 may be included in the composition in an amount of about 5 to 25 wt % for the entire content of the liquid crystal composition. In an implementation, the liquid crystal compound represented by Chemical Formula 14 may be included in the composition in an amount of about 0.03 to 5 wt % for the entire content of the liquid crystal composition. The liquid crystal compounds represented by Chemical Formula 15 to Chemical Formula 19 may be included in an amount suitable to satisfy the physical properties required by the liquid crystal composition.

In an implementation, the liquid crystal compound represented by Chemical Formula 1 may be included in an amount of, e.g., about 1 to 20 wt %, based on the total weight of the liquid crystal composition. In an implementation, at least one among the compounds represented by Chemical Formula 2 to 19 may be included in the liquid crystal composition to satisfy the above-described content, thereby providing the liquid crystal composition for the liquid crystal display having a predetermined physical property.

In an implementation, the dielectric anisotropy ($\Delta\epsilon$) of the liquid crystal composition may be, e.g., −3 to −4, and the rotation viscosity ($\gamma 1$) of the liquid crystal composition may be, e.g., about 50 to about 120. In an implementation, the refractive anisotropy ($\Delta n$) of the liquid crystal composition may be, e.g., 0.08 to 0.15, and the phase transition temperature (Tni) may be, e.g., about 55 to 130° C.

The above-described liquid crystal composition may have negative dielectric anisotropy, and may include the liquid crystal compounds representing the low rotation viscosity such that improved response speed may be provided.

Next, constituent elements of the liquid crystal display including the above-described liquid crystal layer will be described in detail with reference to FIG. 1 and FIG. 2.

First, the lower panel 100 is described.

A gate conductor including a gate line 121 and a voltage dividing reference voltage line 131 may be formed on an insulating substrate 110 formed of transparent glass, plastics, or the like.

The gate line 121 may include a first gate electrode 124a, a second gate electrode 124b, and a third gate electrode 124c.

The voltage dividing reference voltage line 131 may include first storage electrodes 135 and 136, and a reference electrode 137. Second storage electrodes 138 and 139 that are not connected to the voltage dividing reference voltage line 131 may be positioned to overlap a second subpixel electrode 191b.

A gate insulating layer 140 may be positioned on the gate line 121 and the voltage dividing reference voltage line 131.

A first semiconductor layer 154a, a second semiconductor layer 154b, and a third semiconductor layer 154c may be positioned on the gate insulating layer 140. A plurality of ohmic contacts 163a. 165a, 163b, 165b, 163c, and 165c may be formed on the semiconductors 154a, 154b, and 154c.

A data conductor including a data line 171 connected to a first source electrode 173a and a second source electrode 173b, a first drain electrode 175a, a second drain electrode 175b, a third source electrode 173c, and a third drain electrode 175c may be positioned on the ohmic contacts 163a, 165a, 163b, 165b, 163c, and 165c and the gate insulating layer 140.

The data conductor and the underlying semiconductor layers 154a, 154b, and 154c and ohmic contacts 163a, 165a, 163b, 165b, 163c, and 165c may be simultaneously formed by using one mask.

The first gate electrode 124a, the first source electrode 173a, and the first drain electrode 175a may form a first thin film transistor along with the first semiconductor layer 154a, the second gate electrode 124b, the second source electrode 173b, and the second drain electrode 175b form a second thin film transistor along with the second semiconductor layer 154b, and the third gate electrode 124c, the third source electrode 173c, and the third drain electrode 175c form a third thin film transistor along with the third semiconductor layer 154c.

The second drain electrode 175b may be connected with the third source electrode 173c, and includes an extended portion 177 that is widely extended.

A first passivation layer 180p may be formed on the data conductors 171, 173c, 175a, 175b, and 175c and exposed portions of the semiconductors 154a, 154b, and 154c. The first passivation layer 180p may include an inorganic insulating layer, such as a silicon nitride or a silicon oxide.

A color filter 230 may be positioned on the first passivation layer 180p. The color filter 230 may be extended in a vertical direction along two adjacent data lines. In an implementation, the color filter 230 may be positioned in the lower panel 100 or the color filter 230 may be positioned in the upper panel 200.

A second passivation layer 180q may be positioned on the color filter 230. The second passivation layer 180q, like the first passivation layer 180p, may include the inorganic insulating layer such as a silicon nitride or a silicon oxide.

The second passivation layer 180q may help prevent the color filter 230 from being peeled, and may help suppress contamination of the liquid crystal layer 3 by an organic material such as a solvent flowing in from the color filter 230, thereby preventing defects such as an afterimage that may occur when a screen is driven.

The first passivation layer 180p and the second passivation layer 180q may have a first contact hole 185a and a second contact hole 185b respectively exposing the first drain electrode 175a and the second drain electrode 175b.

The first passivation layer 180p, the second passivation layer 180q, and the gate insulating layer 140 may have a third contact hole 185c exposing a part of the reference electrode 137 and a part of the third drain electrode 175c, and the third contact hole 185c may be covered by a connecting member 195. The connecting member 195 may electrically connect the reference electrode 137 and the third drain electrode 175c that are exposed through the third contact hole 185c.

A plurality of pixel electrodes 191 may be positioned on the second passivation layer 180q. The pixel electrode 191 may be one field generating electrode, and each pixel electrode 191 may include a first subpixel electrode 191a and the second subpixel electrode 191b that may be separated from each other with the gate line 121 interposed therebetween, and may be adjacent in a column direction based on the gate line 121.

The pixel electrode 191 may be made of a transparent material such as ITO or IZO.

The overall shape of the first subpixel electrode 191a and the second subpixel electrode 191b may be a quadrangle, and they respectively may include a cross-shaped stem having a transverse stem 193 and a longitudinal stem 192 that are crossed. In an implementation, the first subpixel electrode 191a and the second subpixel electrode 191b may be respectively divided into a first sub-region Da, a second sub-region Db, a third sub-region Dc, and a fourth sub-region Dd by the transverse stem 193 and the longitudinal stem 192, and each of the sub-regions Da-Dd include a plurality of minute branches.

The first subpixel electrode 191a and the second subpixel electrode 191b may be respectively connected to the first drain electrode 175a and the second drain electrode 175b through the first contact hole 185a and the second contact hole 185b, respectively, and may receive the data voltage from the first drain electrode 175a and the second drain electrode 175b, respectively. In this case, a part of the data voltage applied to the second drain electrode 175b may be divided through the third source electrode 173c, so that a magnitude of the voltage applied to the first subpixel electrode 191a may be larger than that of the voltage applied to the second subpixel electrode 192b.

In this case, sides of the minute branches 194 may distort an electric field and form a horizontal component that determines an inclination direction of the liquid crystal molecules 31. The horizontal component of the electric field may be almost horizontal to the sides of the first to fourth minute branches 194. Accordingly, the liquid crystal molecules 31 may be inclined in a direction parallel to the longitudinal direction of the minute branches 194. One pixel electrode 191 may include four subregions Da to Dd in which longitudinal directions of the minute branches 194 are different from each other, and the directions in which the liquid crystal molecules 31 are inclined are about four directions, and four domains, in which the alignment directions of the liquid crystal molecules 31 are different from each other, may be formed in the liquid crystal layer 3. As described above, when the inclination direction of the liquid crystal molecules is diversified, a reference viewing angle of the liquid crystal display may be increased.

The first subpixel electrode 191a and the second subpixel electrode 191b, to which a data voltage is applied, may generate an electric field together with a common electrode 270 of the upper panel 200, thereby determining orientation of the liquid crystal molecules 31 of the liquid crystal layer 3 between the two electrodes 191 and 270. Luminance of light passing through the liquid crystal layer 3 may vary depending on the determined orientation of the liquid crystal molecules 31.

The aforementioned description of the thin film transistor and the pixel electrode 191 is just an example, and a structure of the thin film transistor and a design of the pixel electrode can be modified to improve side visibility.

A first alignment layer 11 may be positioned on the pixel electrode 191, and the first alignment layer 11 may be a vertical alignment layer. The first alignment layer 11 may be formed to include at least one among general materials used as a liquid crystal alignment layer such as a polyamic acid or a polyimide.

Next, the upper panel 200 will be described.

A second substrate 210 may be positioned to be separated from the first substrate 110. A light blocking member 220 may be positioned between the second substrate 210 and the liquid crystal layer 3. The light blocking member 220 may be positioned in the upper panel 200 to overlap a region where the data line 171 of the lower panel 100 is positioned and a region where the thin film transistor is positioned. In an implementation, the light blocking member 220 may be positioned in the upper panel 200 or may be positioned in the lower panel 100.

Next, an overcoat 250 may be positioned between the light blocking member 220 and the liquid crystal layer 3. In an implementation, the overcoat 250 may be omitted.

Next, the common electrode 270 that is one of the field generating electrodes may be positioned between the overcoat 250 and the liquid crystal layer 3. As the common electrode 270 generates the electric field along with the pixel electrode 191 of the lower panel 100, the direction of the liquid crystal molecules 31 of the liquid crystal layer 3 may be determined.

A second alignment layer 21 may be positioned between the common electrode 270 and the liquid crystal layer 3, and the second alignment layer 21 may be a vertical alignment layer. The second alignment layer 21 may be formed of the same material as the first alignment layer 11.

The liquid crystal layer 3 may be positioned between the first alignment layer 11 and the second alignment layer 21. The liquid crystal layer 3 may include the liquid crystal composition according to an exemplary embodiment having the negative dielectric anisotropy. The liquid crystal molecules 31 of the liquid crystal layer 3 may be aligned to be perpendicular to the surfaces of the two display panels 100 and 200 with respect to their long axes when no electric field is applied.

In an implementation, the liquid crystal layer 3 of the display according an exemplary embodiment may include a compound such as monomer or the like which is cured by polymerization due to light such as ultraviolet rays, or the like. The compound may be the reactive mesogen polymerized by light such as ultraviolet rays, or the like.

The above-mentioned reactive mesogen may be polymerized depending on a manufacturing process to thereby form a polymer, and the liquid crystal molecules 31 are aligned so as to have a pre-tile by the polymer.

Next, the physical properties of an Example liquid crystal composition including the liquid crystal compound represented by Chemical Formula 1 and a Comparative Example liquid crystal composition without it are compared with each other.

The following Example and Comparative Example are provided in order to highlight characteristics of one or more embodiments, but it will be understood that the Example and Comparative Example are not to be construed as limiting the scope of the embodiments, nor is the Comparative Example to be construed as being outside the scope of the embodiments. Further, it will be understood that the embodiments are not limited to the particular details described in the Example and Comparative Example.

TABLE 1

| Chemical Formula | Content (wt %) |
|---|---|
|  | 3-25 |
|  | 3-25 |
|  | 5-20 |
|  | 5-25 |
|  | 3-25 |
|  | 5-30 |
|  | 5-25 |
|  | 10-30 |
|  | 5-15 |
|  | 5-30 |
|  | 5-25 |

TABLE 2

| Chemical Formula | Content (wt %) |
| --- | --- |
|  | 3-25 |
|  | 3-25 |
|  | 5-20 |
|  | 5-25 |
|  | 3-25 |
|  | 5-30 |
|  | 5-25 |
|  | 10-30 |
|  | 5-15 |
|  | 5-30 |
|  | 5-25 |

The Example liquid crystal composition according to Table 1 includes the liquid crystal compound represented by Chemical Formula 1, and the Comparative Example liquid crystal composition according to Table 2 is the liquid crystal composition in which the liquid crystal compound represented by Chemical Formula 1 is not included.

As a result of examining the physical properties of each liquid crystal composition, in the Example liquid crystal composition according to Table 1, the refractive anisotropy ($\Delta n$) was about 0.105, the dielectric anisotropy ($\Delta \epsilon$) was about −3.22, the rotation viscosity ($\gamma 1$) was about 119, and the phase transition temperature (Tni) was about 74° C.

In the Comparative Example liquid crystal composition according to Table 2, the refractive anisotropy ($\Delta n$) was about 0.106, the dielectric anisotropy ($\Delta \epsilon$) was about −3.13, the rotation viscosity (γ1) was about 124, and the phase transition temperature (Tni) was about 74° C.

For example, the Example liquid crystal composition including the compound represented by Chemical Formula 1 may provide the low rotation viscosity while maintaining almost the same level as the Comparative Example liquid crystal composition for other physical properties. Accordingly, the response speed of the liquid crystal display including the Example liquid crystal composition may be improved.

By way of summation and review, the liquid crystal display may include a liquid crystal material that is suitable to control the transmittance of light and obtain desired images. For example, according to the various uses of the liquid crystal display, various characteristics such as low voltage driving, a high voltage holding ratio (VHR), a wide viewing angle characteristic, a wide range of operation temperature, and high speed response may be desirable.

The embodiments may provide a liquid crystal composition having a low rotation viscosity. Also, a response speed that is improved through the liquid crystal display including the same may be provided.

According to an embodiment, the liquid crystal composition having the low rotation viscosity may be provided, and the response speed of the liquid crystal display including the same may be improved.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

DESCRIPTION OF SYMBOLS

110: first substrate
210: second substrate
3: liquid crystal layer
31: liquid crystal molecule

What is claimed is:

1. A liquid crystal composition comprising a liquid crystal compound represented by Chemical Formula 1 below:

Chemical Formula 1 wherein, in Chemical Formula 1,
$X_1$ to $X_4$ are each independently hydrogen, fluorine, or an alkyl group, at least one of $X_1$ and $X_2$ being fluorine and at least one of $X_3$ and $X_4$ being fluorine,
$Z_1$ and $Z_2$ are each independently a single bond, a double bond, $CF_2CF_2$, or $OCF_2$, $R_1$ is hydrogen, fluorine, or an alkyl group,
$R_2$ is hydrogen, fluorine, an alkyl group, or an alkoxy group,
A is

D is

B is cyclohexane, cyclohexene, or benzene,
C is cyclopentane or cyclopentene,
$X_5$, $X_6$, $X_7$, and $X_8$ in A and D are each independently hydrogen, fluorine, or an alkyl group,
p is an integer of 1 to 4, and
q is an integer of 0 to 3.

2. The liquid crystal composition as claimed in claim 1, wherein the liquid crystal compound represented by Chemical Formula 1 includes a liquid crystal compound represented by one of Chemical Formula 1-1 to 1-4:

Chemical Formula 1-1

Chemical Formula 1-2

Chemical Formula 1-3

Chemical Formula 1-4

3. The liquid crystal composition as claimed in claim 1, wherein:
  a dielectric anisotropy (Δ∈) of the liquid crystal compound represented by Chemical Formula 1 is −4 to −5, and
  a rotation viscosity (γ1) of the liquid crystal compound represented by Chemical Formula 1 is about 150 or less.

4. The liquid crystal composition as claimed in claim 3, wherein:
  a phase transition temperature (Tni) of the liquid crystal compound represented by Chemical Formula 1 is 95° C. to 105° C., and
  a refractive anisotropy (Δn) of the liquid crystal compound represented by Chemical Formula 1 is 0.2 to 0.3.

5. The liquid crystal composition as claimed in claim 1, further comprising a liquid crystal compound represented by one of Chemical Formula 2 to Chemical Formula 19:

Chemical Formula 2

Chemical Formula 3

Chemical Formula 4

Chemical Formula 5

Chemical Formula 6

Chemical Formula 7

Chemical Formula 8

Chemical Formula 9

Chemical Formula 10

Chemical Formula 11

Chemical Formula 12

Chemical Formula 13

Chemical Formula 14

Chemical Formula 15

Chemical Formula 16

Chemical Formula 17

-continued

Chemical Formula 18

Chemical Formula 19 wherein, in Chemical Formula 2 to Chemical Formula 19, X and Y are each independently a C1 to C4 alkyl group.

6. The liquid crystal composition as claimed in claim 5, wherein a dielectric anisotropy (Δ∈) of the liquid crystal composition is −3 to −4.

7. The liquid crystal composition as claimed in claim 5, wherein a rotation viscosity (γ1) of the liquid crystal composition is about 120 or less.

8. A liquid crystal display, comprising:
a first substrate;
a second substrate separated from and overlapping the first substrate; and
a liquid crystal layer positioned between the first substrate and the second substrate,
wherein the liquid crystal layer includes a liquid crystal compound represented by Chemical Formula 1:

Chemical Formula 1 wherein, in Chemical Formula 1,
$X_1$ to $X_4$ are each independently hydrogen, fluorine, or an alkyl group, at least one of $X_1$ and $X_2$ being fluorine and at least one of $X_3$ and $X_4$ being fluorine,
$Z_1$ and $Z_2$ are each independently a single bond, a double bond, $CF_2CF_2$, or $OCF_2$,
$R_1$ is hydrogen, fluorine, or an alkyl group,
$R_2$ is hydrogen, fluorine, an alkyl group, or an alkoxy group,
A is -continued

D is

B is cyclohexane, cyclohexene, or benzene,
C is cyclopentane or cyclopentene,
$X_5$, $X_6$, $X_7$, and $X_8$ in A and D are each independently hydrogen, fluorine, or an alkyl group,
p is an integer of 1 to 4, and
q is an integer of 0 to 3.

9. The liquid crystal display as claimed in claim 8, wherein the liquid crystal compound represented by Chemical Formula 1 includes a liquid crystal compound represented by one of Chemical Formula 1-1 to 1-4:

Chemical Formula 1-1

Chemical Formula 1-2

Chemical Formula 1-3

-continued

Chemical Formula 1-4

10. The liquid crystal display as claimed in claim 8, wherein:
   a dielectric anisotropy (Δ∈) of the liquid crystal compound represented by Chemical Formula 1 is −4 to −5, and
   a rotation viscosity (γ1) of the liquid crystal compound represented by Chemical Formula 1 is about 150 or less.

11. The liquid crystal display as claimed in claim 10, wherein:
   a phase transition temperature (Tni) of the liquid crystal compound represented by Chemical Formula 1 is 95° C. to 105° C., and
   a refractive anisotropy (Δn) of the liquid crystal compound represented by Chemical Formula 1 is 0.2 to 0.3.

12. The liquid crystal display as claimed in claim 8, wherein the liquid crystal layer further includes a liquid crystal compound represented by one of Chemical Formula 2 to Chemical Formula 19:

Chemical Formula 2

Chemical Formula 3

Chemical Formula 4

Chemical Formula 5

Chemical Formula 6

Chemical Formula 7

Chemical Formula 8

Chemical Formula 9

Chemical Formula 10

Chemical Formula 11

Chemical Formula 12

Chemical Formula 13

Chemical Formula 14

Chemical Formula 15

Chemical Formula 16

Chemical Formula 17

Chemical Formula 18

Chemical Formula 19 wherein, in Chemical Formula 2 to Chemical Formula 19, X and Y are each independently a C1 to C4 alkyl group.

13. The liquid crystal display as claimed in claim 12, wherein a dielectric anisotropy (Δ∈) of the liquid crystal composition is −3 to −4.

14. The liquid crystal display as claimed in claim 12, wherein a rotation viscosity (γ1) of the liquid crystal composition is about 120 or less.

15. The liquid crystal display as claimed in claim 8, further comprising:
   a thin film transistor on the first substrate;
   a pixel electrode connected to the thin film transistor; and
   a common electrode forming an electric field with the pixel electrode.

16. The liquid crystal display as claimed in claim 15, wherein the pixel electrode includes a cross-shaped stem and a minute branch extending from the cross-shaped stem.

* * * * *